United States Patent [19]

Wada et al.

[11] 4,042,393
[45] Aug. 16, 1977

[54] SILVER HALIDE EMULSION CONTAINING TWO EQUIVALENT TYPE COUPLER FOR USE IN PHOTOGRAPHY

[75] Inventors: Hajime Wada; Shouji Kikuchi; Haruo Hori; Takaya Endo, all of Hino, Japan

[73] Assignee: Konishiroku Photo Industry Co., Ltd., Tokyo, Japan

[21] Appl. No.: 615,825

[22] Filed: Sept. 22, 1975

Related U.S. Application Data

[63] Continuation-in-part of Ser. No. 482,748, June 24, 1974, abandoned.

[30] Foreign Application Priority Data

June 22, 1973    Japan .................................. 48-69866

[51] Int. Cl.$^2$ ............................ G03C 7/00; G03C 1/40
[52] U.S. Cl. ........................................ 96/55; 96/56.6; 96/100 R
[58] Field of Search ............................ 96/56.6, 100, 55

[56] References Cited

U.S. PATENT DOCUMENTS

| | | | |
|---|---|---|---|
| 3,737,316 | 6/1973 | Salminen et al. | 96/56.6 |
| 3,942,987 | 3/1976 | Landholm et al. | 96/77 |
| B 351,673 | 1/1975 | Fleckenstein et al. | 96/77 |

*Primary Examiner*—J. Travis Brown
*Attorney, Agent, or Firm*—Bierman & Bierman

[57] ABSTRACT

This invention relates to a method for developing an exposed silver halide color photosensitive material which comprises conducting the development in the presence of the following compound:

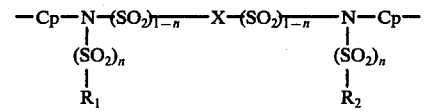

wherein Cp is a cyan coupler residue having been removed one hydrogen atom from active methylene of the coupler; $R_1$ and R2 are individually hydrogen, helogen, a substituted or unsubstituted group selected from an aliphatic hydrocarbon residue, an aromatic hydrocarbon residue, acyl, carbamoyl, cyans and formyl; X is a substituted or unsubstituted group selected from an aliphatic hydrocarbon residue, an aromatic hydrocarbon residue, a heterocyclic ring residue, and a carbonyl group; and *n* is 0 or 1 provided that, when *n* is 1, X is the carbonyl group.

7 Claims, No Drawings

SILVER HALIDE EMULSION CONTAINING TWO EQUIVALENT TYPE COUPLER FOR USE IN PHOTOGRAPHY

This application is a continuation-in-part of co-pending U.S. Ser. No. 482,748, filed June 24, 1974, now abandoned, which claims the priority of Japanese application Ser. No. 69,866 filed June 22, 1973.

DETAILED DESCRIPTION OF THE INVENTION

This invention relates to a novel coupler for use in photography. More particularly, the invention relates to a novel coupler for use in photographic processes using a silver halide as a photosensitive component.

In the art of photography, silver halides are conventionally used for recording of light information because they are excellent in photographic characteristics such as sensitivity and gradation. In order to obtain a colored image the silver halide is generally combined with a certain kind of a color-forming compound which is reacted with a certain kind of a reactive compound to form a dye in correspondence with the information recorded on the silver halide, namely a dye image. This color-forming compound is generally called a coupler, and the reactive compound is a color-forming developing agent such as an aromatic primary amine developing agent.

As is well known in the art, when light is recorded imagewise on a silver halide having a development center and the silver halide is developed in the presence of a coupler with a developing agent, the developing agent reduces the silver halide to reduced silver, and the developing agent per se is oxidized to form an active oxidation product of the developing agent and this oxidation product reacts with the coupler to form a dye, with the result that a dye image corresponding with the information recorded on the silver halide is formed.

The reaction between the coupler and developing agent is performed on the active position of the coupler, and the active position redides generally at an active methine or methylene group in the molecule of the coupler.

A coupler having a hydrogen atom at this active position is caled a 4-equivalent coupler, and a coupler having at this active position a group capable of being readily split at the rection between the coupler and developing agent, namely a so called split-off group, is called a 2-equivalent coupler.

In the case of a 4-equivalent coupler, at the reaction of the coupler with the developing agent, 4-equivalents of a silver halide having the center of development are required per active position, but in the case of a 2-equivalent coupler only 2-equivalents of a silver halide are required. Therefore, the 2-equivalent coupler provides a dye image of a higher concentration than the 4-equivalent coupler, when compared based on the same amount of developed silver. Further, in the case of the 2-equivalent coupler, if a group bonding the split-off group (bonding group) is chosen appropriately, it is possible to impart a development-inhibiting activity to a compound formed by splitting of the split-off group. For example, a 2-equivalent coupler having a split-off group with a this group (—s—) as the bonding group is called a development inhibitor-relasing coupler (D. I. R. coupler) and since this coupler inhibits the development in proportion to the amount of developed silver, it can be applied in various manners. For example, this D. I. R. coupler exhibits so called intra-image effects in its own layer, such as effects of controlling the image tone and finely dividing the image particles, and so-caled interimage effects on other layers, such as effects of improving the dye hue. Further, the coupler of this type has various function on other layers. By virtue of these effects and functions, the coupler of this type is also utilized to the diffusion transfer type photography.

Still in addition. Some 2-equivalent type couplers, for instance, those in which a dye component is included in the splet-off group can be used in the diffusion transfer type photography and in this case, the split dye is utilized for formation of an image of a diffused dye on an image-receiving layer. A coupler of this type is called a diffusible dye-releasing coupler (D. D. R. coupler). Further, some colored 2-equivalent couplers have a masking effect of correcting the color of the dye image, and a coupler of this type is called a colored coupler.

Because of the foregoing substantial advantages over 4-equivalent couplers and various applicabilities, 2-equivalent couplers tend to be used more frequently than 4-equivalent couplers.

Although heretofore known 2-equivalent couplers ae excellent over 4-equivalent couplers in various characteristics, they are still insufficient in the dye-forming rate and they are likely to cause fogs or contaminations in a silver halide-containing photosensitive layer. They are also defective in that they cannot be dispersed in a photosensitive layer at a sufficient dispersion concentration. Improvement of these defects of 2-equivalent type couplers has been sought in the art.

It is a primary object of this invention to provide a novel 2-equivalent type coupler in which the foregoing defects involved in conventional 2-equivalent type couplers are overcome.

Another object of this invention is to provide a 2-equivalent type coupler having excellent photographic characteristics.

Still another object of this invention is to provide a silver halide photosensitive material including such 2-equivalent type coupler and a photographic process using such 2-equivalent type coupler.

This invention more specifically relates to a two equivalent photographic cyan coupler representative by the following formula [I]

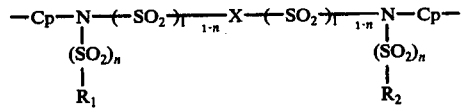

wherein Cp is a cyan coupler residue having been removed one hydrogen atom from active methylene of the coupler being of phenol or naphthol having carbamoyl or acylamino at the second position thereof; $R_1$ and $R_2$ are individually hydrogen, halogen or a substituted or unsubstituted group selected from an aliphatic hydrocarbon residue, an aromatic hydrocarbon residue, acyl, carbamoyl, cyano and formyl; X is a substituted or unsubstituted group selected from an aliphatic hydrocarbon residue, an aromatic hydrocarbon residue, a heterocyclic ring residue and carbonyl; and $n$ is 0 or 1 provided that, when $n$ is 1, X is the carbonyl group.

The above 2-equivalent type coupler of this invention has one or more split-off group which has a sulfoamide or sulfamyl group, the sulfoamide or sulfamyl group bonding the coupler residue and the split-off group, so the coupler is high in a dye formation speed, does not causes fogs, color contamination and the like in photosensitive layers, and is further more well-dispersed at high concentration in layers such as photosensitive layers of photographic elements.

In addition, dyes derived from the coupler are excellent in stability against heat humidity and light as well as in light absorption characteristics in which the dyes show us absorption of unnecessary light but good absorption of necessary light. Moreover, the coupler does not restrain a development unlike a certain kind of known two equivalent couplers.

For instance, silver halide photographic light sensitive material containing two equivalent couplers of this invention can be thinner and improved in color, resolution power and sharpness. Further more, since they are improved in transparency for layers under a layer containing the couplers, sensitivity is improved in a multi layer light sensitive materials.

In this invention, the cyan coupler residue shown as Cp in the aforementioned formula [I] preferably has a phenol or naphthol ring as a body structue unit, which ring can have various substituents preferably attaching to the second position of the phenol or α-naphthol ring. In other words, the cyan coupler residue is preferably of phenol or α-naphthol having substituents at the second position thereof, the substituents being halogen, or a substituted or unsubstituted carbamoyl or acylamino, are hydrogen having been removed from active methilene (hereinafter called active position) of the phenol or naphthol.

Two-equivalent couplers having other spirt-off groups such as halogen and aryloxy are well known as cyan couplers in photography. However those couplers have souse drawbacks which are removed in this invention.

Since the two equivalent couplers of this invention are of a peculiar structure, they shown more excellent photographic results than those disclosed in U.S. P. 3737316.

The coupler of this invention has generally a split-off group on the fourth position of a phenol or naphthol group.

Representative examples of coupler residues in which split-off group is detached (called as cyan coupler residue herein after) is represented by the following general formula [II] [III] and [IV]

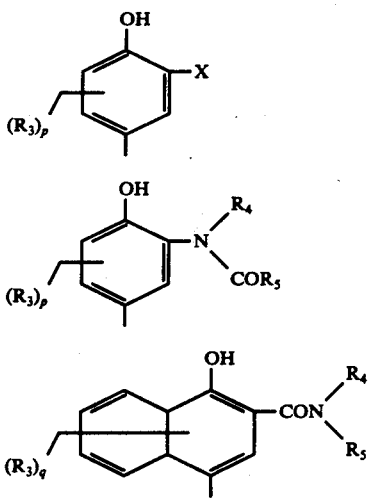

wherein $R_3$ stands for a hydrogen or halogen atom, an aliphatic hydrocarbon residue or a group $-O-R_6$ or $-S-R_6$ in which $R_6$ is an aliphatic hydrocarbon residue, and when a plurality of groups $R_3$ are present in one molecule, they can be the same or different and further the hydrocarbon residue can have a substituent; $R_4$ and $R_5$ stand for a member selected from aliphatic or aromatic hydrocarbon residues, and heterocyclic-ring residues or one of them can be a hydrogen atom, these groups can have a substituent, and $R_4$ and $R_5$ can form together a nitrogen-containing heterocyclic-ring; $p$ is an integer of 1 to 3; and $q$ is an integer of 1 to 5.

In the foregoing formulate, the aliphatic hydrocarbon residue can be either saturated or unsaturated, and it can be straight, branched or cyclic. Preferred examples of the aliphatic hydrocarbon residue include alkyl groups such as methyl, ethyl, isobutyl, tertial octhyl, dodecyl, octadecyl, cyclobutyl cyclopentyl, cyclohexyl, 2-norbornyl, and alkenyl groups such as allyl, iso-propenyl, and ethenyl. Typical examples of the aryl group are phenyl and naphthyl groups, and typical examples of the hetero-ring residue are of a 5- or 6 member ring including Nitrogen, sulfor, oxygen and/or hetero atoms as a member and such as pyridyl, quinolyl, thienyl, piperidyl and imidazolyl, oxadiazolyl groups. As the substituent to be introduced into such aliphatic, aryl or heterocyclic-ring residue, there can be mentioned halogen nitro, hydroxyl, carboxyl, amino, a substituted amino group, a sulfo group, and substituted and unsubstituted alkyl, alkenyl, aryl, heterocyclic-ring, alkoxy, alkythio, aryloxy, arylthio, arylazo, acylamino, carbamoyl, ester, acyl, acyloxy, sulfoneamide, sulfamoyl, sulfonyl, morpholino, peperidyl piperazyl and imidazolyl groups. As the hetero-ring formed by $R_5$ and $R_6$, there can be preferably used the above-exemplified nitrogen-containing hetero-rings. As the specific examples of the acyl group in the above general formula [I], there can be mentioned an acetyl, propionoyl, butylyl or benzoyl group which can be substituted with halogen, nitro, alkyl, alkenyl, aryl, alkoxy or aryloxy. As the typical instances of the carbamoyl group, there can be mentioned alkylamino-carbonyl such as methylaminocarbonyl, ethylaminocarbonyl or dodecylaminocarbonyl; aryl aminocarbonyl such as anilinocarbonyl or naphtylaminocarbonyl which can be substituted with halogen, nitro, amino, aryl, acylamino, alkyl, alkenyl, aryl, alkoxy or aryloxy. As the substituted amino group, there can be mentioned an alkyl amino or arylamino such as methylamino, propion amino, anilino or naphtylamino.

Preferred examples of the split-off group other than Cp in the above general formula [I] is illustrated below.

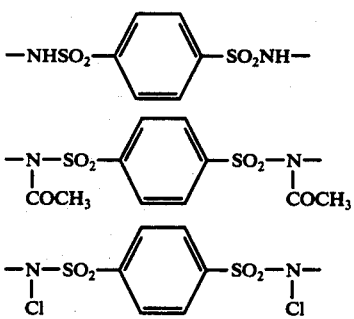

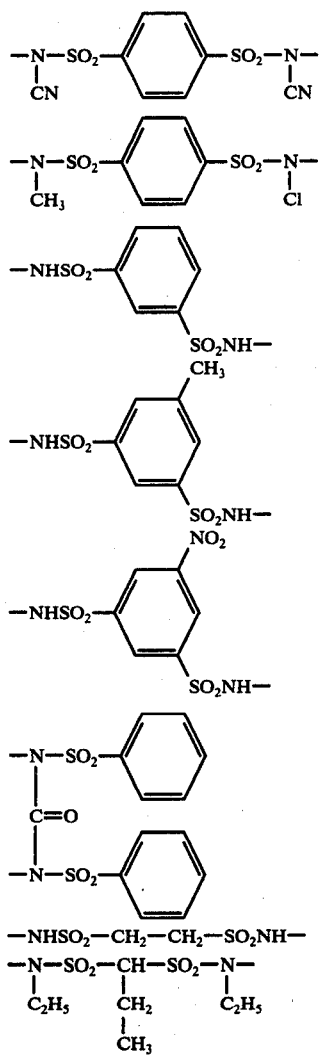
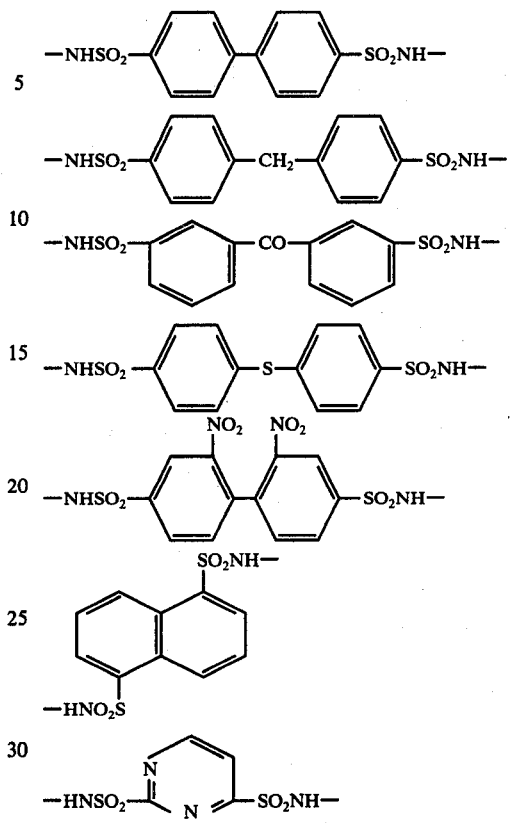
The couplers of this invention have a coupling group (sprit-off group) between the two bodies and therefore show excellent photographic characteristics as mentioned before: The couplers according to this invention are examplified hereinafter but the scope of this invention is not limited by the examples.
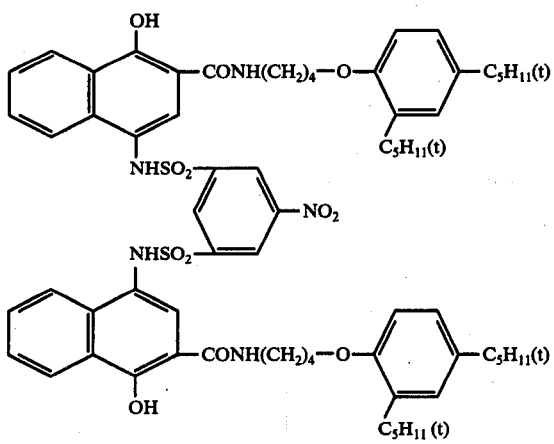

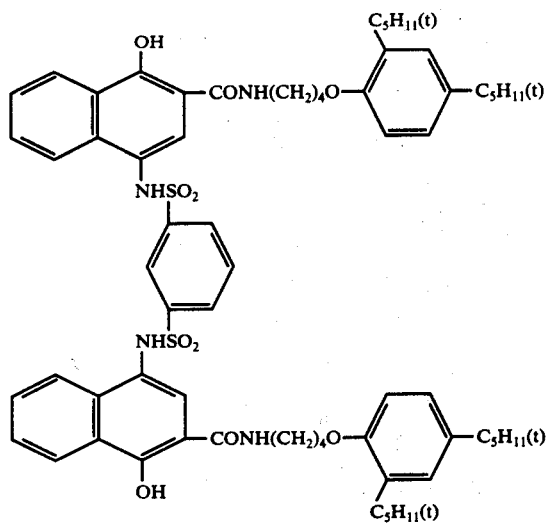
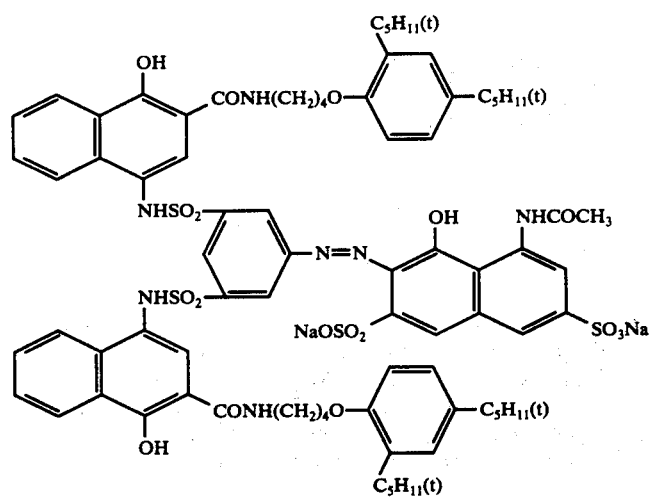
(3)
(4)
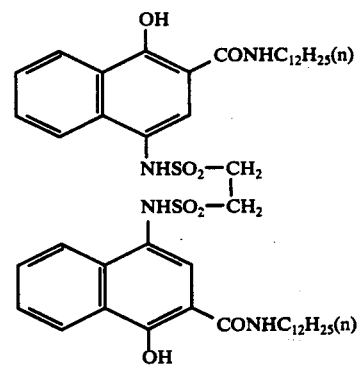
(5)
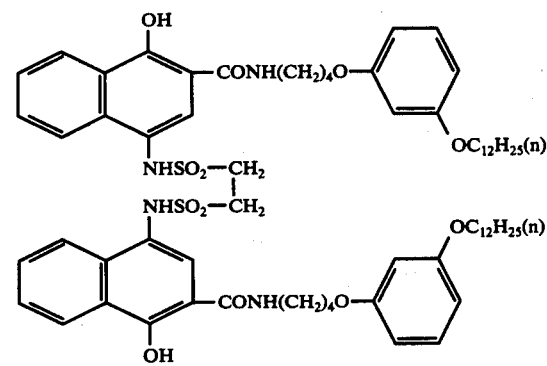

(6)
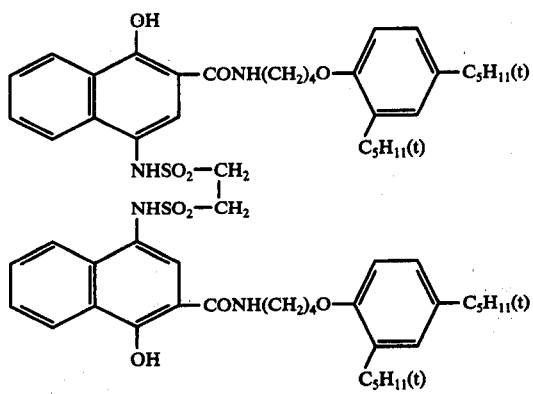
(7)
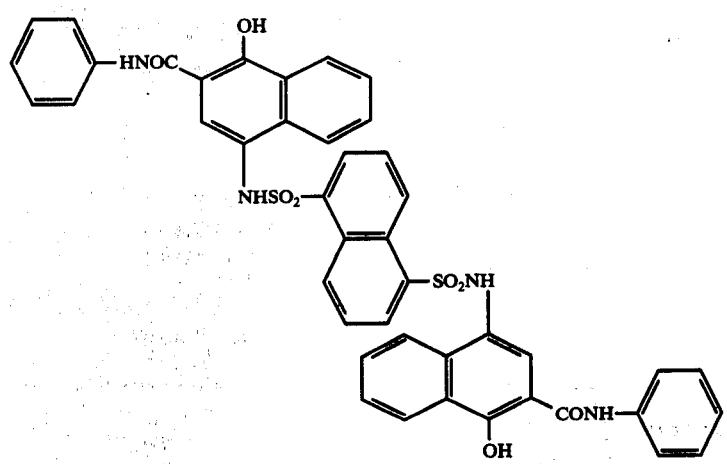
(8)
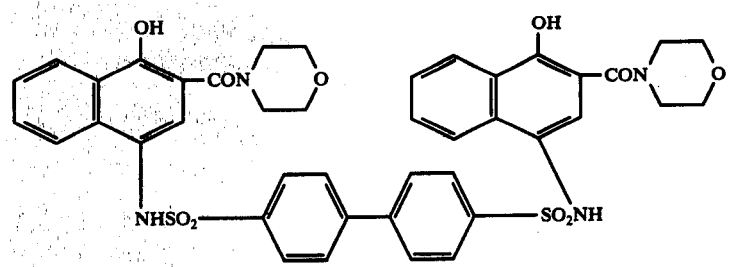
(9)

-continued
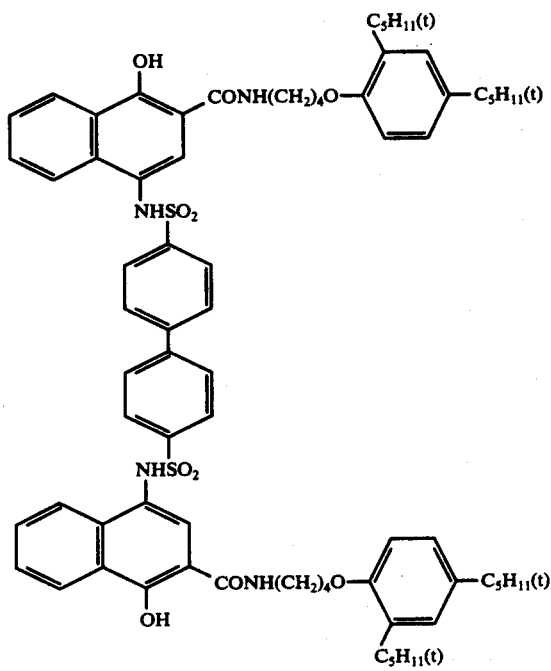
(10)
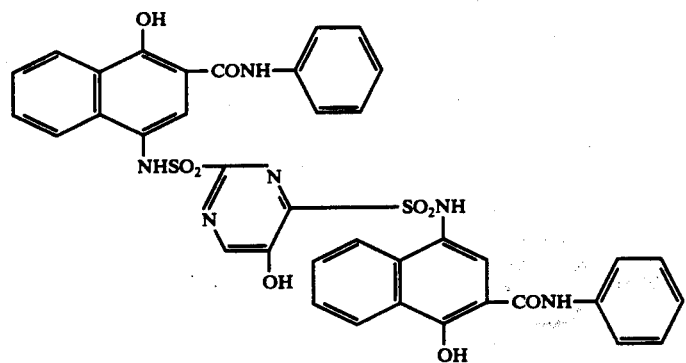
(11)
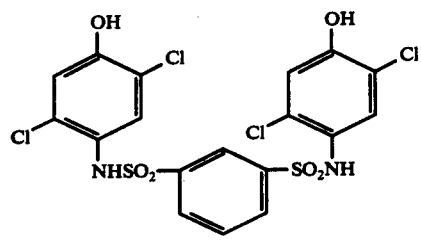

-continued

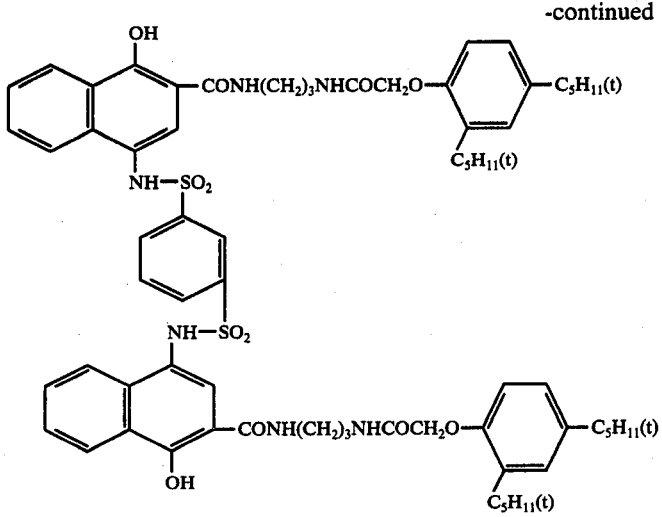

(12)

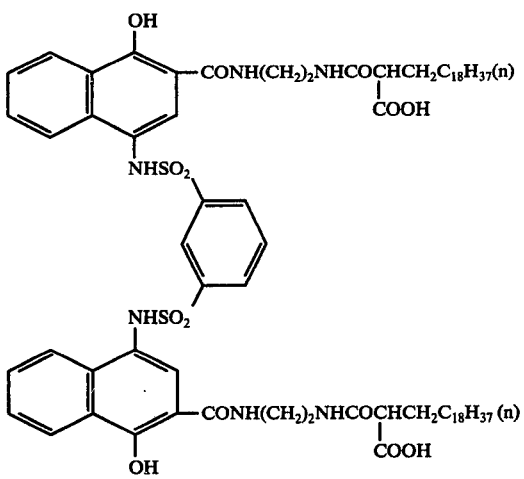

(13)

The compound according to this invention is synthesized by reacting, at a room temperature or more a naphthol type cyan coupler having amino at the forth position thereof, for example, 1-hydroxy-4-amino-N-[δ-(2, 4-di, tert-amylphenoxy) butyl-2-naphthoamide, 1-hydroxy-4-amino-N-(2-tetradecyloxyphenyl)-1-naphthoamide] or a phenol type cyan coupler, for example, 6-chloro-5-methyl-4-amino-2-acetoamidephenol, 2, 5-di-chloro-4-aminophenol and alkyl or arylsulfochoride in the solution of benzene or acetone in the presence of a dehydrogenchloride agent such as sodium carbonate and pyridine then cristalizing the filtrated substance in a solvent of ethanol or benzene.

Synthetic examples of the coupler according to this invention are illustrated below.

SYNTHESIS EXAMPLE 1

Syntheses of Examplified Coupler (1)

0.02 mole of 1-hydroxy-4-amino-N-[δ-(2, 4-di, tert amylphenoxy)butyl]-2-naphthoamide and 0.01 mole of 5-nitro-1, 3-benzendisulfochloride were dissolved into 200 ml of dried benzene.

And then 0.03 mole of pyridine was added into the so-prepared solution and the resulting solution was stirred for 3 hours at 50° C. After completion of the reaction, a solvent was removed under reduced pressure, and then filtration was conducted by addition of ethanol to obtain crystals which was recrystalized by the use of benzene. The melting point of resulting cristals was 194° ~ 195° C. The yield was 85%. It was found from the result of elementary analysis that the resulted compound was coupler (2).

SYNTHESIS EXAMPLE 2

Synthesis of Examplified Coupler (2)

0.02 mole of 4-amino-1-hydroxy-N-[δ-(2, 4-di, tert amylphenoxy)butyl]-2-naphthoamide and 0.01 mole of m-benzenedisulfochrolide were dissolved into 100 ml of dried benzene and 0.03 mole of pyridine was added into the resulting solution. The resulting solution was refluxed for 3 hours.

After the completion of the reaction, the solvent was removed under reduced pressure, an ethanol was added to the residue and filtration was conducted thereafter to obtain crystals which were than recrystalized so that a compound having a melting point of 203° to 204° C (the yield 80%) was obtained.

It was found from the result of elementary analysis that the resulted compound was coupler (2).

SYNTHESIS EXAMPLE 3

Synthesis of Examplified Coupler (3)

0.01 mole of coupler (1) was dissolved into 150 ml of acetone and 5g of powdery zinc oxide was added into the resulting solution. The mixture of 6 ml of concentrated hydrochrolic acid and 6 ml of water was dropped into the resulting liquid being stirred at 15° C. Three hours thereafter, unsoluble materials were removed from the liquid by filteration and the filtered liquid was concentrated under reduced pressure. The concentrated was dissolved into ether and the resulting was washed by equeous sodium carbonate. It was additionally washed by water and then dried by the use of anhydrous sodium sulfate. The solvent was than removed from it under reduced pressure and the remaining cyrupy material was dissolved in the mixture of 10 ml of 2N-hydrochloric acid and 30 ml of acetone. The resulting being cooled and stirred was then diazotized by the use of aqueous sodium nitrite. The obtained diazorium salt solution was added into an aqueous liquid containing 0.015 mole of acetyl H-acid, so that pink dyes were obtained. Those dyes were filtered off, washed by water, and dried, so a compound having a melting point of more than 300° C inclusive was obtained with 76% of yield.

This was found coupler (3) from the result of elementary analysis.

SYNTHESIS EXAMPLE 4

Synthesis of Examplified Coupler (9)

0.02 mole of 4-amino-1-hydroxy-N-[δ-(2, 4-di-tert-amylphenoxy)butyl]-2-naphthoamide and 0.01 mole of 4, 4'-Biphenyl disulfochloride were dissolved into 200 ml of dried benzene. 0.03 mole of pyridine was then added to the resulting solution and the resulting was refluxed for five hours. After the completion of the reaction, the solvent was removed under reduced pressure and 90% alcohol was added to the resulting. This was kept as it was for a while and crystals were obtained by filteration thereafter. The crystals were recrestalized from the mixture of acetone and alcohol to obtain crystals having a decomposed point of 129° C with 64% of yield.

This compound was found coupler (9) from the result of elementary analysis.

Various couplers can be synthesized according to methods similar to those described in the foregoing Synthesis Examples, and among these various couplers, those exemplified above are chosen and the results of the elementary analysis of them are shown below.

conventional couplers having a relatively analogous structure, the couplers of this invention can easily be dispersed in a protective colloid such as a gelatin. Among the couplers of this invention, oil-soluble couplers have an excellent solubility in coupler solvents, and couplers having a hydrophilic group exhibit excellent characteristics in Fischer dispersion. The couplers of this invention can easily be added to a liquid developer (these coupler are called as external coupler herein after). By virtue of these excellent characteristics, especially when the couplers of this invention are incorporated into photosensitive layers of photographic photosensitive materials, the thickness of the photosensitive layer can be greatly reduced, the sharpness and other properties or resulting dye images can be improved, and no bad interaction is shown in color development (these coupler are called as internal coupler hereinafter). Still further, by virtue of good reactivity, color contamination and the like can be highly improved with use of the couplers of this invention.

As pointed above, dyes obtained by employing the couplers of this invention have excellent color absorption characteristics.

As apparent from the foregoing description, the couplers of this invention have various applicabilities and they are used for attaining various objects by choosing a suitable combination of a coupler body and a split-off group. For example, couplers having a water-soluble group such as sulfonyl and carboxyl in the cyan coupler residue have good dispersibility, and couplers in which the bonding group-containing split-off group per se has dispersibility can be used as diffusible couplers. These couplers are utilized in the so called external photography coupler-in-developer type and can be incorporated into, for example, a color-forming liquid developer. For instance, coupler (11) can be mentioned as a coupler of this type.

Couplers of this invention in which the cyan coupler residue has dispersibility, the split-off group has appropriate non-dispersibility because it has such a non-dispersible group such as an aliphatic long-chain hydrocarbon residue, e.g., octadecyl but the entire structure consisting of such cyan coupler residue and split-off

| COUPLER | CALCULATED VALUE | | | ACTUALLY OBTAINED VALUE | | |
| --- | --- | --- | --- | --- | --- | --- |
| Number | C | H | N | C | H | N |
| 1 | 66.48 | 7.07 | 5.70 | 65.89 | 6.80 | 5.56 |
| 2 | 69.01 | 7.32 | 4.73 | 69.11 | 7.49 | 4.14 |
| 3 | 59.14 | 5.91 | 6.11 | 58.25 | 5.37 | 5.42 |
| 4 | 64.38 | 7.89 | 6.25 | 64.01 | 8.04 | 5.97 |
| 5 | 66.73 | 7.75 | 4.58 | 66.91 | 8.00 | 4.21 |
| 6 | 67.69 | 7.64 | 4.93 | 68.33 | 6.87 | 4.54 |
| 7 | 65.32 | 3.99 | 6.92 | 70.07 | 4.24 | 7.65 |
| 8 | 61.29 | 4.66 | 6.80 | 61.38 | 4.99 | 6.85 |
| 9 | 70.54 | 7.21 | 4.44 | 68.83 | 7.11 | 4.29 |
| 10 | 56.63 | 3.38 | 12.16 | 56.09 | 3.92 | 11.55 |
| 11 | 44.35 | 2.48 | 5.74 | 44.33 | 2.53 | 5.80 |
| 12 | 66.22 | 6.99 | 6.62 | 65.87 | 7.40 | 6.94 |
| 13 | 54.33 | 8.02 | 6.02 | 65.91 | 7.57 | 6.32 |

The so obtained couplers of this invention are characterized by a high dye-forming speed and they exhibit, as mentioned above, a much higher dye-forming speed in color development than conventional 4-equivalent type cyan couplers. Further, their dye-forming speed is higher than that of a 2-equivalent type coupler having as a split-off group aryloxy such as phenoxy and nitro-phenoxy or that of a 2-equivalent type coupler having as a split-off group an ester-linkage group such as acetoxy and benzoyloxy. Moreover, as compared with group has dispersibility, can be utilized in the external photography as well as the above-mentioned type couplers.

Couplers (7), (8), and (10) can be mentioned as preferred couplers for the external photography in addition to the above-mentioned coupler (11).

As is well known in the art, in the external photography, a coupler is incorporated into a color-forming liquid developer, and a coupler-free photosensitive material, especially a silver halide photosensitive material for black-white photography (prepared for the external photography), is exposed to light and developed with the coupler-containing color-forming liquid developer. On the development, both of the color-forming developing agent and the coupler intrude into the photosensitive material and the color-forming developing agent reacts with the diffusible coupler in the presence of a silver halide having a development center, with the result that a dye image is formed. In order to obtain a multicolor image, the development is generally carried out by employing successively color-forming liquid developers containing different couplers (for example, a cyane coupler, a magenta coupler and a yellow coupler).

Such color-forming liquid developer can comprise, in addition to the color-forming developing agent and coupler, various photographic additives used in ordinary color-forming liquid developers, such as sulfites, carbonates, bisulfites, bromides and iodies of alkali metals, and the like. A typical instance of the composition of such liquid developer is as follows:

| Composition of Color-Forming Liquid Developer: | |
|---|---|
| Color-forming developing agent | 1 – 5 g |
| Anhydrous sodium sulfite | 1 – 3 g |
| Anhydrous sodium carbonate | 10 – 60 g |
| Potassium bromide | 0.5 – 1.5 g |
| Coupler | 1 – 3 g |
| Water | balance |
| Total | 1 liter |

An external color-forming liquid developer containing a coupler of this invention, especially one suitable for the external photography such as mentioned above, has a good solubility as compared with liquid developers comprising conventional couplers and exhibits excellent properties such as mentioned above.

Couplers in which the cyan coupler residue is diffusible, the split-off group is diffusible but the entire coupler structure is non-diffusible; couplers in which the cyan coupler residue is non-diffusible, the split-off group is diffusible but the entire coupler structure is non-diffusible; and couplers in which the cyan coupler residue is non-diffusible, the split-off group is diffusible and the entire coupler structure is diffusible; are suitable for use in the diffusion transfer type photographic precess. Imparting diffusibility to each group can be accomplished by selecting a low-molecular-weight group and or introducing a water-soluble hydroxyl group such as sulfenyl and the like. Imparting non-dispersibility to each group can be accomplished by introducing a long-chain aliphatic hydrocarbon residue and or selecting a relatively high-molecular-weight group.

As a specific instance of the coupler to be used for the diffusion transfer type photography, there can be mentioned couplers in which chemical-seeds unnecessary for image formation at color-forming development though either the cyane coupler residue or the split-off group is diffusible. For example, couplers formed by introducing a hydroquinone residue, a resorcin residue or the like into either of the cyan coupler residue and split-off group through or without an appropriate bonding group can be effectively used for the diffusion transfer type photography, and this means can be applied to other type couplers differing in the combination of dispersibility and non-dispersibility between the cyane coupler residue and split-off group. When the diffusion transfer type photographic process is adopted, the image forming method is divided into two types, one utilizing a cyan dye obtained by the reaction between the cyan coupler residue and the color-forming developing agent, and the other utilizing the split-off group portion splitted off in color development. In the former method, it is necessary that the obtained cyan dye is diffusible, and in the latter method, it is indispensable that a compound formed by isolation of the split-off group from the active position is diffusible. When such isolated compound is utilized, it is necessary that said compound should be colored. In short, such compound includes a dye content such as an azo dye. Examples of the split-off group of this type are represented by the following general formula [VII]:

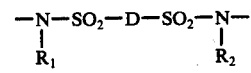

wherein $R_1$ and $R_2$ are as defined above and $R_1$ and $R_2$ can be D, and D stands for a specific residue included in the definition of X set forth before, the residue being more specifically a residue of a dye.

In the general formula [VII], the dye residue D has preferably a water-soluble group and it is preferred that the dye residue D is a divalent residue of a dye selected from azo dyes, azomethine dyes, indoaniline dyes, indophenol dyes and anthraquinons dyes.

As the coupler suitable for the diffusion transfer type photographic process, there can be mentioned, for example, couplers (3).

As is well known in the art, a combination of a photosensitive material and an image-receiving material is employed in the diffusion transfer type photography, and according to this photographic method, after exposure of the photosensitive material, it is superposed on the image-receiving material at least during the development step to form an image on the image-receiving material. For instance, a coupler-containing silver halide photosensitive material is used in combination with an image-receiving material comprising an image-receiving layer formed on a support through an undercoat layer, an intermediate layer and the like. After exposure of the silver halide photosensitive material is suparposed on the image-receiving layer of the image-receiving material, if desired, through a protective layer, and a color-forming liquid developer is intruded into the clearance between the two layers to effect development. Thus, the dye formed on the photosensitive layer is transferred onto the image-receiving layer by diffusion, and finally, the image-recerining material is peeled off from the photosensitive material, whereby a dye image is formed on the image-receiving material. Various methods are known as such diffusion transfer type photographic process. For instance, there can be mentioned a method in which the photosensitive material is integrated with the image-receiving material and the steps of superposing the image-receiving material and photosensitive material and peeling off the image-receiving material from the photosensitive material are omitted. In this method, if a boundary layer between the image-receiving material and photosensitive material or a layer adjacent thereto is an opaque layer, a support for the photosensitive material is transparent and ligh exposure is effected from the side of the support of the photosensitive material. If a boundary layer or a layer adjacent thereto is substantially transparent, in order for the resulting image not to be influenced by the image formed in the photosensitive material, at least one of the above layers should be specified at the step conducted after the light exposure, for instance, at the color-forming development step, and in this type combination of the image-receiving material and photosensitive material, at least a support on the side of the image-receiving material should be transparent and the light exposure is effected from the side of the image-receiving material. After the light exposure, a color-forming liquid developer is intruded into the boundary between the photosensitive material and image-receiving material or in the vicinity thereof, and an image is formed on the image-receiving layer.

In another diffusion transfer type photographic method, a color-forming liquid developer is retainer in advance in an image-receiving material, and the development and transfer treatments are performed only by superposing such image-receiving material on a photosensitive material.

Couplers of this invention can be applied effectively to any of known diffusion transfer photographic methods. In general, the coupler is incorporated in a photosensitive material and use of a silver halide photosensitive material is preferred. The coupler is generally used in an amount of about 0.07 to about 0.7 mole, preferably 0.1 to 0.4 mole, per mole of the silver halide.

A coupler known as the so called internal couplers used in the state incorporated in a photosensitive material, especially a silver halide photosensitive material. In order not to impose influences on other layers, it is preferred that the coupler to be used is non-diffusible. Among couplers to be used for the above-mentioned diffusion transfer photography, those that are non-diffusible can also be used effectively. It is preferred that a coupler in which the cyan coupler residue is non-diffusible and the split-off group is either diffusible or non-diffusible is used as the internal coupler.

Preferred instances of the coupler of this type are couplers (1), (2), (3), (4), (5), (6), (9) and (12).

Some internal couplers are substantially colorless and are ordinary couplers capable of forming a dye by the reaction with an oxidation product of the color-forming developing agent formed at the development step. Other internal couplers are colored couplers and are preferably used for color correction in the so called masking process. For color correction in the masking process, couplers (3) is preferably employed. In color correction in the masking process, the color of the colored coupler per se is decolorized or is excluded from the system of the photosensitive material at color-forming development, and simultaneously, a cyan dye is formed by its reaction with a color-forming developing agent. In general, a colored coupler of this type is used in combination with a substantially colorless coupler.

Internal couplers are divided into two types depending on whether they contain, in the molecule, a hydrophilic group or an oleophilic group. Namely, they are divided into the Fischer dispersion type which is incorporated in the form of an alkaline liquid into a coating composition for formation of a photosensitive layer and the protect type which is incorporated in the state dissolved in a coupler solvent. As the former type, there can be typically mentioned coupler (13). When the couplers of this invention are dispersed by appropriate means depending on the above-mentioned types, they exhibit a much higher solubility than conventional couplers, and hence, they can provide such advantages as formation of a higher density image, improvement of the layer transparency and the resolving power.

In case a coupler of this invention is incorporated into a photosensitive material, it is generally used in an amount of about 0.07 to about 0.7 mole, preferably 0.1 to 0.4 mole, per mole of a silver halide. In case a coupler of this invention is used for color correction in the masking process or it is used for improving characteristics of other coupler or for other purposes, the coupler is generally used in an amount of about 0.01 to about 0.1 mole, preferably about 0.03 to about 0.07 mole, per mole of a silver halide.

As described hereinabove, couplers of this invention can be applied in various manners depending on intended purposes, and they exhibit excellent characteristics in each application.

A preferred photosensitive material to which the coupler of this invention is applied is a silver halide photosensitive material, and the coupler of this invention can be used for various silver halide photosensitive materials. For example, the coupler of this invention can be used for silver halide photosensitive materials for the above-mentioned diffusion transfer type photography, ordinary negative photosensitive materials, ordinary reversal photosensitive materials, ordianry positive photosensitive materials, direct positive photosensitive materials, special photosensitive materials (such as photosensitive materials for printing, X-ray photosensitive materials, high resolving power photosensitive materials, infrared photosensitive materials and ultraviolet photosensitive materials), and other silver halide photosensitive materials.

As the silver halide to be used for such photosensitive materials, there can be mentioned, for example, silver chloride, silver iodide, silver iodobromide, silver chlorobromide, silver chloroiodobromide, etc. These silver halides are prepared according to various methods such as the neutral method, the ammonia method, the simultaneous mixing method and conversion method, and a suitable method is chosen depending on the intended type of the photosensitive material. In the case of a mixed silver halide, the mixing ratio or two or more of silver halides is appropriately chosen. For example, a silver halide having a relatively low sensitivity and a relatively fine particle size is composed mainly of silver chloride, and the content of silver chloride is reduced in a mixed silver halide having a relatively high sensitivity. As the silver halide used for a direct positive photosensitive material, there can be mentioned, for example, Herschel reversal type silver halide and solarization type silver halides, and in general, appropriate chemical or optical fogs are imparted in advance to these silver halides. Further, these silver halides are chemically sinsitized by active gelatin; sulfur sensitizers such as allylthiocarbamide, thiourea and cysteine selenium sensitizers; reducing sensitizers such as stannous salts and polyamines; and noble metal sensitizers such as gold sensitizers, e.g., potassium aurithiocyanate, cerium chloroaurate and 2-aurosulfobenzothiazole methochloride, and sensitizing amounts of water-soluble salts of ruthenium, rhodium, iridium and the like, e.g., ammonium chloropalladate, potassium chloroplatinate and sodium chloropalladide (some of hese sensitizers act as a sensitizer or as a fog inhibitor depending on the amount used). These sensitizers can be used singly or in combination of two or more of them. For example, a combination of a gold sensitizer and a sulfur sensitizer and a combination of a gold sensitizer are used for the chemical sensitization.

Silver halide can be optically sensitized in a desired wavelength region. For example, they can be optically sensitized (for example, hypersensitized) by one or more of cyanine dyes such as zeromethine dyes, monomethine dyes, dimethine dyes and trimethine dyes, merocyanine dyes, and other optical sensitizers.

Such silver halide is dispersed in a suitable protective colloid to form a photosensitive layer. As the protective colloid to be used for formation of a photosensitive layer and other structural layers such as an intermediate layer, a protective layer, a filter layer, an image-receiving layer and a pH-adjusting layer (for example, an undercoat of the image-receiving layer), gelatine is generally employed, and in addition, there are employed colloidal albumin, cellulose derivatives, polyvinyl compounds (for example, polyvinyl alcohol) and other synthetic resins. They can be used singly or in the form of a mixture of two or more of them. Further, it is possible to employ acetyl cellulose having an acetyl content of about 19 to about 26% or water-soluble ethanolamine cellulose acetate in combination with the foregoing protective colloids.

As the support of a photosensitive material, there can be employed paper, laminated paper (for example, a laminate of polyethylene and paper), glass, and a film or sheet of such a substrate as cellulose actage, cellulese nitrate, polyester, polycarbonate, polyamide, polystrene and polyolefin. In order to improve the adhesive property of such support to each structural layer, the support can be subjected to various surface treatments for rendering it hydrophilic. For example, the support can be subjected to the saponification treatment, the corona discharge treatment, the undercoat treatment, the setting treatment and the like.

A photosensitive material comprises at least a support and a photosensitive layer formed thereon. In general, a photosensitive material has a multilayer structure composed of at least several layers in which suitable layers are so disposed at various positions as to attain objects such as mentioned above. For example, a photosensitive material for color photography can include at least two photosensitive layers sensitized in different wavelength regions and each photosensitive layer can contain a coupler to form a color different from the color of the coupler contained in the other photosensitive layer.

Since a cyan coupler residue portion is utilized in the coupler of this invention, a cyan dye is formed, and the cyan coupler of this invention is used for a photosensitive material for color photography in combination with other 2-equivalent and 4-equivalent type couplers such as magenta couplers, e.g., 5-pyrazolenes, and yellow couplers having active methylene inserted between two carbonyl groups. In a pseudo-color photosensitive material, the coupler of this invention can be used singly or in combination with a similar cyan coupler, and the relation between the sensitive wavelength region and the color of dyes drived from the coupler does not always accord with such relation as found in an ordinary color photosensitive material.

A photosensitive layer sensitive to a certain wavelength region may comprise two or more layers differing in the sensitivity, and couplers forming the same color but differing in the type, for example, a combination of 2-equivalent type and 4-equivalent type couplers, can be incorporated into respective layers. Such multilayer photosensitive layer is adopted for further improving the resolving power or attaining other objects.

As pointed above, the coupler of this invention can be combined with other 2-equivalent type or 4-equivalent type couplers. For example, so called colored couplers (having a split-off group including as a bonding group an azo group at the active point), so called D. I. R. couplers (releasing a development inhibitor at the development step) and the like can be combined as the 2-equivalent type coupler.

A photographic photosensitive material can additionally contain various photographic additives in the photosensitive layer and/or other structural layers (such as intermediate, undercoat, filter, protective and image-receiving layers), and as such photosensitive additives, there can be employed, for example, stabilizers such as mercury compounds, triazoles, azaindenes, zinc salts and cadmium salts; sensitizers such as quaternary ammonium salts and polyethylene glycol; film property-improving agents such as gylcerin, dihydroxalkanes, esters ethylene-bis-glycolic acid and emulsions or dispersions of polymers; film-hardening agents such as formaldehyde, halogen-substituted fatty acids, disulfonyl chloride, bisaziridine and ethyleneimines; extenders such as saponin, lauryl and oleyl monothers of polyethylene glycol and sulfated and alkylated polyethylene gylcol salts; organic solvents such as coupler solvents (high-boiling-point organic solvents and/or low-boiling point organic solvents, for example, dibutyl phthalate, tricrezyl phosphate, acetone, methanol, ethanol and ethylene cellosolve); so called D. I. R. compounds capable of releasing a development inhibitor and forming a substantially colorless compound at the development step; antistatic agents; deforming agents; ultraviolet adsrorbers; fluorescent whitening agents; stop-preventive agents, matting agents; halation-preventive agents and irradiation-reventive agents. These photographic additives can be used singly or in combination.

An image-receiving material which is an individual layer independent from a photosensitive material and is used for the diffusion transfer type photography in combination with a photosensitive material comprises at least an image-receiving layer formed on such a support as mentioned above, and it may further comprise a protective layer, an undercoat layer, a pH-adjusting layer and the like according to need. Each layer comprises a protective colloid such as mentioned above as a layer-forming material, and various photographic additives such as mentioned above can be imcorporated there-in according to need. For example, in order to prevent re-diffusion of a diffusible dye diffused from the photosensitive layer or color bleeding at the color development of the image-receiving layer, it is desired that a compound having a capacity of catching a dye or a compound having an ability to annul the dispersibility of a dye is incorporated into the image receiving layer. It is also possible to incorporate such compound into a layer adjacent to the image-receiving layer. Typical instances of such compound are mordants such as polymers of an aminoguanidine derivative of vinylmethylketone disclosed in U.S. Pat. No. 2,882,156 and mordants disclosed in U.S. Pat. No. 3,271,148 and 2,271,147 and pH-adjusting agents such as inorganic and organic acids.

As pointed above, a color-forming liquid developer for color formation and development of an exposed photosensitive material comprises a developing agent as a main ingredient. As the developing agent, there are typically employed p-phenylenediamines such as diethyl-p-phenylenediamine hydrochoride, monomethyl-p- phenylenediamine hydrochloride, dimethyl-p-phenylenediamine hydrochloride, 2-amino-5-diethylaminotoluene hydrochloride, 2-amino-5-(N-ethyl-N-dodecylamino) -toluene, N-ethyl-N-β-methanesulfonamidoethyl-3-methyl-4-aminoaniline sulfate, N-ethyl-N-β-methanesulfonamidoethyl-4-aminoamiline, 4-N-ethyl-N-β-hydroxy-ethylaminoaniline and the like.

These developing agents can be used singly, or mixtures of two or more of them may be used. These developing agents can be used, if desired, in combination with developing agents for black-white photography, such as hydroquinone and the like. Further, these developing agents for color photography can contain alkalis such as sodium hydroxide, ammonium hydroxide, sodium carbonate, sodium sulfate and sodium sulfite and other various additives such as alkali metal halides, e.g., potassium bromide and development-adjusting agent e.g., citrazinic aicd. In some diffusion trasfer type photographic methods, this developing agent for color photography is incorporated in advance into an image-receiving material. In such methods, the color-forming developing agent is separated from the alkali, and only one of the developing agent and alkali is incorporated into the image-receiving layer and it is treated with a liquid containing the other component at the development step.

The coupler of this invention reacts with an oxidation product of the color-forming developing agent formed on development of a silver halide with such color-forming liquid developer to form a cyan dye, and some couplers provide other dyes (inclusive of cyane dyes).

In case the silver halide contained in the photosensitive material or developed silver is removed outside the system after such color-forming development treatment, a fixing liquid, a bleaching liquid, a combination of a fixing liquid and a bleaching liquid, a bleaching-fixing liquid and the like are employed. Treatments with these liquids are conducted in combination with other treatments such as water-washing treatment, stopping treatment, stabilizing liquid treatment and the like. As the fixing component, there can be employed, for example, solvents for silver halides such as sodium thiosulfate and ammonium thiosulfate, and as the bleaching component, there can be employed, for example, red prussiate, and ammonium, ferric and sodium salts of ethylenediamine tetraacetic acid.

This invention is as detailed hereinabove, and the coupler of this invention is superior to conventional 2-equivalent type couplers in various photographic characteristics.

This invention will now be described more detailedly by reference to the following Examples which do not limit the scope of this invention.

EXAMPLE 1

10 g of a coupler as indicated in Table 1 given below was added to a liquid mixture of 20 ml of dibutyl phthalate and 60 ml of ethyl acetate, and the mixture was heated at 60° C. to dissolve the coupler completely. The resulting solution was mixed with 5 ml of a 10% aqueous solution of Alkanol B (alkylnaphthalene sulfonate manufactured by Du Pont) and 200 ml of a 5% aqeous solution of gelatin, and the mixture was emulsified by means of a colloid mill to form a coupler dispersion.

The so formed dispersion was added to 500 g of a gelatin emulsion for negative including silver iodobromide (containing 6.0 mole % of silver iodide), and the mixture was coated and dried on a cellulose triacetate film base.

The so obtained sample was exposed to light and developed at 20° C. for 10 minutes with a color-forming liquid developer having the following composition:

| | |
|---|---|
| N-ethyl-N-β-methanesulfonamidoethyl-3-methyl-4-aminoaniline sulfate | 5.0 g |
| Anhydrous sodium sulfite | 2.0 g |
| Sodium carbonate (monohydrate) | 50.0 g |
| Potassium bromide | 1.0 g |
| Sodium hydroxide | 0.55 g |
| Benzyl alcohol | 4.0 ml |
| Water | balance |
| Total | 1 liter |

The so treated sample was subjected to customary stopping and fixing treatments and washed with water for 10 minutes. Then, the sample was bleached at 20° C. for 5 minutes with a bleaching liquid having the following composition:

| | |
|---|---|
| Red prussiate | 100 g |
| Potassium bromide | 50 g |
| Water | balance |
| Total | 1 liter |

Then, the sample was washed with water for 5 minutes, and subjected to the fixing treatment at 20° C. for 5 minutes by employing a fixing liquid having the following composition:

| | |
|---|---|
| Sodium thiosulfate (pentahydrate) | 250 g |
| Water | balance |
| Total | 1 liter |

The sample was washed with water for 25 minutes and then dried.

The so treated sample was tested with respect to photographic characteristics to obtain results shown in Table 1.

Table 1

| Sample No. | Coupler Used | Relative Sensitivity | γ-Value | Maximum Density (Dmax) | Absorption Maximum Wavelength (max) | Image Photo-resistance | Moisture Resistance |
|---|---|---|---|---|---|---|---|
| 1 | coupler (1) | 195 | 1.75 | 2.53 | 700 nm | 94 % | 78 % |
| 2 | coupler (9) | 175 | 1.70 | 2.45 | 700 nm | 93 % | 77 % |
| 3 | comparative coupler (1) | 100 | 1.58 | 2.28 | 700 nm | 91 % | 74 % |

In the above Table, the value of the sensitivity is a relative value calculated based on the sensitivity (100) of the sample 3 using comparative coupler (1) disclosed in the specification of U.S. Pat. No. 3,737,316, which has the following structure:

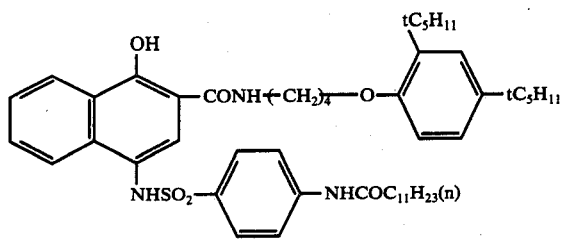

The photo-resistance of each sample was determined by subjecting each resulting image to exposure for 16 hours by employing a xenon fadometer and expressing the residual density in terms of the percentage based on the density (100) before the exposure. The moisture resistance was determined by storing the resulting image under a condition of a relative humidity of 80% for 2 weeks and expressing the residual density in terms of the percentage based on the density (100) before the storage test.

As is apparent from the results shown in Table 1, the coupler of this invention shows excellent photographic characteristics (high sensitivity, excellent photo-resistance, excellent moisture resistance and the like), and a sample using the coupler of this invention provides a dye image having a high sharpness.

When the above procedures were repeated by employing couplers (2), (4) and (6) instead of couplers (1) and (9), it was found that each of them has similarly excellent photographic characteristics as the internal coupler.

EXAMPLE 2

The photosensitive material including this invention coupler was prepared in the same manner as in Example 1.

The so obtained photosensitive material was exposed to light according to a customary method and developed at 38° C for 3 minutes and 15 secondes with a color-forming liquid developer having the following composition;

| | |
|---|---|
| N-ethyl-N-(β-hydroxyethyl)-3-methyl-4-aminoaniline | 5.0 g |
| Anhydrous Sodium Sulfite | 2.0 g |
| Sodium carbonate | 50.0 g |
| Potassium bromide | 1.0 g |
| Sodium hydroxide | 0.55 g |
| water | balance |
| total | 1 liter |

Then the sample was bleached at 38° C. for 6 minuts with a bleaching liquid having the following composition:

| | |
|---|---|
| Sodium ethylenediamino tetreacetate | 40.0 g |
| Ferric chloride | 30.0 g |
| Sodium carbonate(monobydrate) | 20.0 g |
| Potassium bromide | 30.0 g |
| Water | balance |
| total | 1 liter |

Then the sample was water-washed for 2 minuts and stabilized in a stabilizing liquid and then dried to obtain an excellent cyan image. In rapid process was obtained excellent color image.

EXAMPLE 3

10 g of coupler as shown in the table 2 was added to a liquid mixture of 20 ml of tricresyl phosphate and 60 ml of ethyl acetate and the mixture was heated at 60° C. to dissolve the coupler completely. The resulting solution was incerporated into 200 ml of a 5% aqueous solution of gelatin together with 5 ml of a 10%, aqueous solution of Alkanol B. The mixture was emulsified by means of a coloid mill to form a coupler dispersion.

The resulting dispersion was added to a red-sensitive, highly sensitized emulsion of silver iodobromide (containing 4.0 mole % of silver iodide), and the mixture was coated and dried on a cellulose film base to obtain a photosensitive material having a stable coating.

In the same manner as described in Example 1, this photosensitive material was exposed to light and developed at 21° C. for 12 minutes with a liquid developer having the following composition:

| | |
|---|---|
| Metol | 3.0 g |
| Anhydrous sodium sulfite | 50.0 g |
| Hydroquinone | 6.0 g |
| Sodium carbonate | 40.0 g |
| Potassium bromide | 3.5 g |
| Potassium thiocyanide | 2.0 g |
| Water | balance |
| Total | 1 liter |

The developed sample was subjected to customary stopping, film-hardening and water-washing treatments and it was subjected to secondary exposure to white light.

Then, the sample was subjected to color-forming development at 21° C. for 13 minutes by employing a color-forming liquid developer having the following composition:

| | |
|---|---|
| N,N-diethyl-2-methyl-p-phenylenediamine | 3.0 g |
| Anhydreus sodium sulfite | 4.0 g |
| Sodium carbonate (monohydrate) | 20.0 g |
| Potassium bromide | 2.0 g |
| Water | balance |
| Total | 1 liter |

The sample was subjected to stopping, water-washing, bleaching and fixation according to customary methods, washed for 20 minutes with running water and dried to obtain a positive colored image of a cyane dye excellent in transparency.

This sample was tested and determined to obtain results show in Table 2

Table 2

| Sample No | coupler used | relative speed | Maximum Density Dmax | Absorption Maximum Wovelength λmax | Image photo-resistance | moisture Resistance |
|---|---|---|---|---|---|---|
| 4 | coupler (5) | 131 | 2.45 | 710 | 93 % | 82 % |
| 5 | coupler (12) | 153 | 2.57 | 710 | 92 % | 79 % |

Table 2-continued

| Sample No | coupler used | relative speed | Maximum Density Dmax | Absorption Maximum Wovelength λmax | Image photo-resistance | Image moisture Resistance |
|---|---|---|---|---|---|---|
| 6 | comparative coupler (1) | 100 | 2.30 | 710 | 90 % | 77 % |

As is apparent from the results shown in Table 2, it will readily be understood that the coupler of this invention indicates excellent photographic characteristics also in a reversal photosensitive material.

EXAMPLE 4

2.0 g of coupler (3) of this invention was dissolved in 2.0 ml of tricrezyl phosphate and 6.0 ml of ethyl acetate and a coupler-emulsified dispersion was prepared in the same manner as in Example 1. The resulting dispersion was added to 100 ml of high sensitized silver iodobromide emulsion (contained 6.0 mol of silveriodide) and the mixture was coated and dried on a undercoated polyethylene terephthlate film base to obtain a photosensitive material.

The so obtained photosensitive material was exposed to light according to a customary method and treated in the same manner as in Example 2, and dried to obtain a excellent positive colored image of magenta and cyane dye having an absorption maximum at 700 nm.

When the above procedure were repeated by employing the following comparative coupler (2) instead of the coupler (3), was obtained worse result:

Comparative coupler (2) (set forth in U.S. Pat. No. 3,034,892)

[Structure: naphthol with OH, CONH(CH$_2$)$_4$O-phenyl-(tC$_5$H$_{11}$)$_2$ substituent, and N=N-phenyl-COCH$_3$ azo group]

| | |
|---|---|
| N,N-di-ethyl-2-methyl-p-phenylene diamine | 2.0 g |
| Anhydrate sodium sulfite | 2.0 g |
| Sodium Carbonate (monohydrate) | 20.0 g |
| Potassium bromide | 2.0 g |
| Water | balance |
| Total | 1 liter |

EXAMPLE 5

Coupler (10) of this invention was dissolved in methanol and added into the following external color-forming liquid developers:

A single layer sample of a highly sensitized silver iodobromide emulsion was exposed according to customary methods and developed at 24° C for 3 minutes with the color-forming developer.

The developed sample was water-washed for 4 minutes, bleached for 5 minutes, water-washed for 5 minutes, fixed for 5 minutes, water-washed for 30 minutes and dried according to customary treatment methods. As a result there was obtained a cyane image having an absorption maximum at 700 nm and being excellent in spectral absorption and transparent.

The above test were repeated as to coupler (11) in place of coupler (10) and the same results were obtained.

From the results of this Example, it will readily be understood that the couplers of this invention are also valuable as an external coupler.

EXAMPLE 6

Dispersion A:

Prepared by the same manner as Example 1 except using a solution that 0.15 g of the coupler (3) and 2.0 g of 1hydroxy-N-[δ-(2,4-di-t- amylphenoxy)butyl] -2-naphtoamide which is known are dissolved in the mixture of 2.2 ml of tricresylphosphate and 6.0 ml of ethylacetate.

Dispersion B: 0.2 g of 2-(1-phenyl-5-tetrazolylthio)-4-[δ-2,4-di-t amylphenoxy)acetamide] indanone (a developing inhibitior releasing type compound) is added to the dispersion A.

Dispersion C:

The same dispersion as dispersion B except that 0.1 g of 1-hydroxy-4-(1-phenyl-5-tetrazolylthio)-2-(2-tetradecyloxyphenyl) naphtoamide is employed as a developing inhibitor releasing type coupler instead of that in dispersion B.

Dispersion D:

Same as the dispersion B except that comparative coupler (2) is used instead of the coupler (3).

These dispersions are respectively added to 100 ml of highly red-sensitive silver iodobromide emulsion (7.0 ml % Ag I) and resulted dispersions are coated on the film supports and dried, and thereby, four samples are obtained.

These obtained samples are exposed to light by an ordinary manner and processed by the same manner as in Example 3.

The results of photographic test are shown in Table 3, in which RMS is 1000 times value of standard deviation of densities obtained by scanning the examples by a microdensitometer having an aperture of 2.5 μ, and U 0.5 is spacial frequency when MT factor decreased to 50 %.

Table 3

| Sample | Fog | Relative Sensitivity | ΓValue | Granurality (RMS) | Sharpness (U 0.5) |
|---|---|---|---|---|---|
| A | 0.18 | 100 | 1.00 | 53 | 50 |
| B | 0.12 | 96 | 0.71 | 42 | 42 |
| C | 0.11 | 95 | 0.70 | 44 | 43 |
| D | 0.13 | 90 | 0.67 | 46 | 45 |

As apparent from Table 3, samples B and C exhibit superior gradation, granularity and sharpness when compared with examples A and D.

What is claimed is:

1. A method for developing an exposed silver halide color photosensitive material which comprises conducting the development in the presence of the following compound:

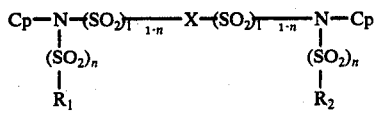

wherein $C_p$ is a phenol or naphthol cyan coupler residue haing one hydrogen atom removed from the active methylene of said coupler; $R_1$ and $R_2$ are individually hydrogen, halogen, and aliphatic hydrocarbon residue, carbamoyl, aromatic hydrocarbon residue, cyano, formyl and acyl; X is pyridyl, quinolyl, thiethyl, piperidyl, imidazolyl, oxydiazolyl,

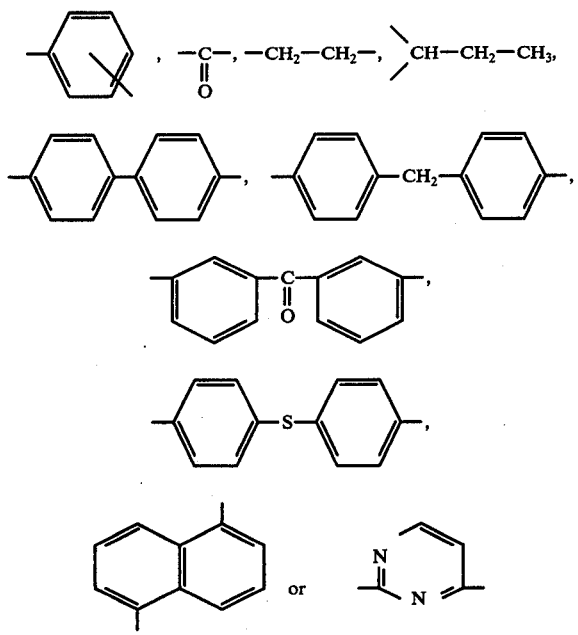

which can be substituted with methyl, nitro, hydroxyl, or

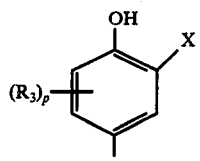

and $n$ is 0 or 1; provided that, when $n$ is 1, X is a carbonyl group.

2. The method according to claim 1 wherein the cyan coupler residue is represented by the following formula [I], [II] or [III]

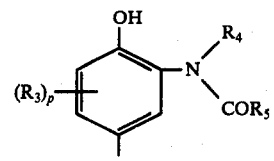

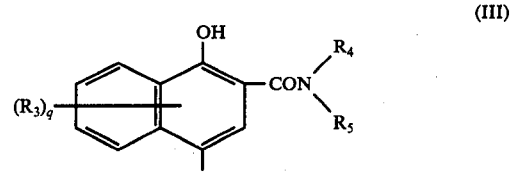

wherein $R_3$ is hydrogen, halogen, an aliphatic hydrocarbon residue, —O—$R_6$ or —S—$R_6$ is an aliphatic hydrocarbon residue, which residue can be substituted with halogen, nitro, hydroxyl, carboxyl, amino, a substituted amino, sulfo, alkyl, alkenyl, aryl, alkoxy, alkylthio, aryloxy, arylthio, arylazo, acylamino, carbamoyl, ester, acyl, acyloxy, sulfonamide, sulfamoyl, sulfonyl, morpholino, piperidyl, piperazyl or imidazolyl; $p$ is an integer of 1 to 3 and each $R_3$ can be the same or different when P is more than 1; $R_4$ and $R_5$ are individually selected from an aliphatic hydrocarbon group, an aromatic hydrocarbon group and a 5 or 6 membered heterocyclic ring group including nitrogen, sulfer and/or oxygen which groups can be substituted with one or more halogen, nitro, hydroxyl, carboxyl, amino, substituted amino, sulfo, alkyl, alkenyl, aryl, alkoxy, alkylthio, aryloxy, arylthio, arylazo, acylamino, carbamoyl, ester, acyl, acyloxy, sulfonamido, sulfamoyl, sulfonyl, morpholino, piperidyl, piperazyl or imidazolyl; $R_4$ and $R_5$ can cooperatively form a hererocyclic ring containing nitrogen; and $q$ is an integer of 1 to 5 inclusive.

3. The method according to claim 1 wherein the aromatic hydrocarbon residue is aryl.

4. The method according to claim 1 wherein the aliphatic hydrocarbon residue is selected from a groups consisting of alkyl and alkenyl.

5. The method according to claim 1 wherein the development is carried out in the presence of at least one p-phenylenediamine.

6. A silver halide color photographic material which comprises a support and a photosensitive layer thereon, the layer comprising silver halide grains and the following compound:

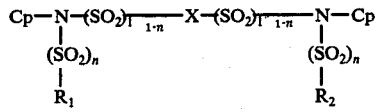

wherein $C_p$ is a phenol or naphthol cyan coupler residue having one hydrogen atom removed from the active methylene of said coupler; $R_1$ and $R_2$ are individually hydrogen, halogen, an aliphatic hydrocarbon residue, carbamoyl, aromatic hydrocarbon residue, cyano, formyl and acyl; X is

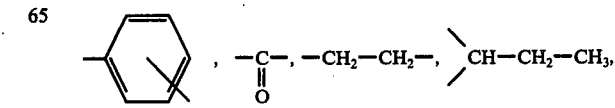

-continued
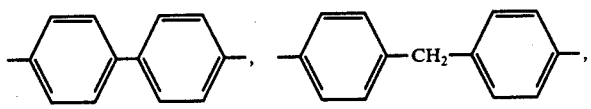
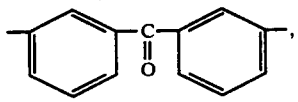
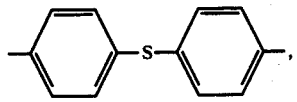
-continued
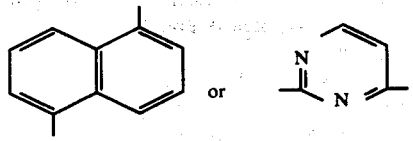
which can be substituted with methyl, nitro, hydroxyl, or
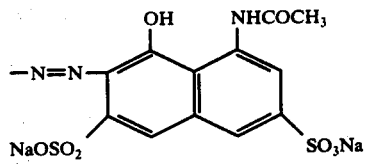
and $n$ is 0 or 1; provided that, when $n$ is 1, X is a carbonyl group.
7. The photosensitive material according to claim 6 wherein the photosensitive material comprises said compound in an amount of 0.01 to 0.7 mole per mole of the silver halide.
* * * * *